(12) United States Patent
Maertens et al.

(10) Patent No.: US 6,521,403 B1
(45) Date of Patent: Feb. 18, 2003

(54) EPITOPES IN VIRAL ENVELOPE PROTEINS AND SPECIFIC ANTIBODIES DIRECTED AGAINST THESE EPITOPES: USE FOR DETECTION OF HCV VIRAL ANTIGEN IN HOST TISSUE

(75) Inventors: Geert Maertens, St. Kruis Brugge; Erik Depla, Destelbergen; Marie-Ange Buyse, Melsen, all of (BE)

(73) Assignee: Innogenetics N.V., Ghent (BE)

( * ) Notice: Subject to any disclaimer, the term of this patent is extended or adjusted under 35 U.S.C. 154(b) by 0 days.

(21) Appl. No.: 09/645,470

(22) Filed: Aug. 24, 2000

Related U.S. Application Data

(63) Continuation of application No. PCT/EP99/02154, filed on Mar. 29, 1999.

(30) Foreign Application Priority Data

Mar. 27, 1998 (EP) .............................. 98870060

(51) Int. Cl.⁷ .................... C12Q 1/70; G01N 33/53; A61K 39/395; A61K 39/42; A61K 39/29
(52) U.S. Cl. .............. 435/5; 435/7.1; 435/7.2; 424/141.1; 424/142.1; 424/143.1; 424/147.1; 424/159.1; 424/228.1; 530/300
(58) Field of Search ............... 435/5, 7.1, 7.2; 424/141.1, 142.1, 143.1, 147.1, 159.1, 228.1; 530/300

(56) References Cited

U.S. PATENT DOCUMENTS

| | | |
|---|---|---|
| 5,308,750 A | 5/1994 | Mahta |
| 5,514,539 A | 5/1996 | Bukh |
| 5,610,009 A | 3/1997 | Watanabe |
| 5,830,691 A | 11/1998 | Miyamura |
| 5,871,962 A | 2/1999 | Bukh |
| 5,919,454 A | 7/1999 | Brechot |
| 6,150,134 A | 11/2000 | Maertens |

FOREIGN PATENT DOCUMENTS

| | | |
|---|---|---|
| WO | PCT/US91/08272 | 1/1991 |
| WO | PCT/IT92/00081 | 1/1992 |
| WO | PCT/US92/07189 | 1/1992 |
| WO | 92 13892 A | 8/1992 |
| WO | WO-9213892 A1 * | 8/1992 |
| WO | PCT/US93/00907 | 1/1993 |
| WO | WO-9318054 A2 * | 9/1993 |
| WO | 93 18054 | 9/1993 |
| WO | 94 05311 A | 3/1994 |
| WO | WO-9405311 A3 * | 3/1994 |
| WO | WO96/04385 | 2/1996 |
| WO | 96 40764 A | 12/1996 |

OTHER PUBLICATIONS

Hiramatsu N. Et Al.: "Immunohistochemical Detection of Hepatites C Virus–Infected Hepatocytes in Chronic Liver Disease with Monoclonal Antibodies to Core, Envelope and NS3 Regions of the Hepatits C Virus Genome" Hepatology, vol. 16, No. 2, 1992, pp. 306–311, XP002084942 abstract p. 308, left–hand column, line 27—right–hand column, line 13.

(List continued on next page.)

Primary Examiner—Hankyel T. Park
Assistant Examiner—Stacy S. Brown
(74) Attorney, Agent, or Firm—Nixon & Vanderhye P.C.

(57) ABSTRACT

Antibodies to two new epitopes on the HCV envelope proteins we, identified which allow routine detection of native HCV envelope antigens, in tissue or cells derived from the host. The new epitopes are: the E1 region aa 307–326 and the N-terminal hyper variable region of E2 aa 395–415. Surprisingly, we characterised an antibody that reacts with various sequences of the hypervariable domain of E2. Specific monoclonal antibodies directed against these epitopes and allowing routine detection of viral antigen are described.

8 Claims, 4 Drawing Sheets

OTHER PUBLICATIONS

Figure 1:
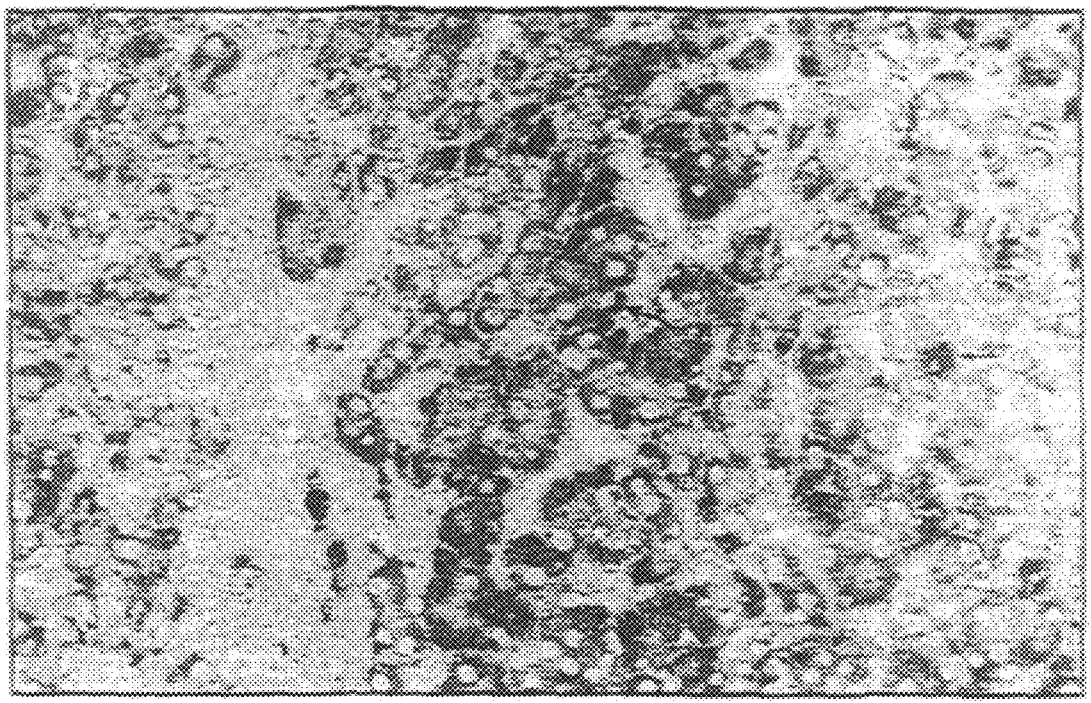

Chan S–W. Et Al.: "Human Recombinant antibodies Specific for Hepatitis C Virus Core and Envelope E2 Peptides from an Immune Phage Display Library" J. General Virology, vol. 77, 1996, pp. 2531–2539, XP002084943 p. 2532, left–hand column, line 32–35 p. 2533; table 1 p. 2537, right–hand column, line 18–27.

Maertens G. Et Al. :"Mapping of Human and Murine B Cell Epitopes on Purified Hepatits C Virus E1 and E2 Proteins" "AASLD Abstracts" Hepatology, vol. 26, No. 4part2, Oct. 1997 (1997–10), p. 186A XP002084941 A232 the whole document.

Suzuki, T. (1) Et Al: "Detection of the E1 protein of HCV in peripheral blood mononuclear cells and in Iymphocyte infiltrates in the liver." Hepatology, (Oct., 1998) vol. 28, No. 4 Part 2, pp. 271A. Meeting Info.: Biennial Scientific Meeting of the International Association for the Study of the Liver and $49^{TH}$ Annual Meeting and Postgraduate Courses of the American Association for TH, XP002116634 the whole document.

Ralston et al., "Characterization of Hepatitis C Virus...," J. Virol 67: 6753–6761 (1993).

Nishihara et al., "Secretion and Purification of Hepatitis C . . . ," Gene 129; 207–214 (1993).

Choo et al., "Vaccination of Chimpanzees Against...Hepititis C Virus," ProcNatl Acad Su 91:1294–1298 (1994).

Lanford et al., "Analysis of Hepititis C Virus...," Virology 197: 225–235 (1993).

* cited by examiner

EPITOPES IN VIRAL ENVELOPE PROTEINS AND SPECIFIC ANTIBODIES DIRECTED AGAINST THESE EPITOPES: USE FOR DETECTION OF HCV VIRAL ANTIGEN IN HOST TISSUE

CROSS REFERENCES TO RELATED APPLICATIONS

This application claims priority per Rule 55 and 35 USC 119 to prior foreign application 98870060.5 EP filed Mar. 27, 1998 and is a continuation of PCT/EP99/02154 filed Mar. 29, 1999.

FIELD OF THE INVENTION

The present invention is based on the finding that antibodies directed against specific epitopes of the E1 and E2 protein of HCV can be used to detect viral antigens in host tissues.

BACKGROUND OF THE INVENTION

Hepatitis C virus (HCV) infection is a major health problem in both developed and developing countries. It is estimated that about 1 to 5% of the world population is affected by the virus. HCV infection appears to be the most important cause of transfusion-associated hepatitis and frequently progresses to chronic liver damage. Moreover, there is evidence implicating HCV in induction of hepatocellular carcinoma. Consequently, the demand for reliable diagnostic methods and effective therapeutic agents is high. Also sensitive and specific screening methods of HCV-contaminated blood-products and improved methods to culture HCV are needed.

HCV is a positive stranded RNA virus of approximately 9,400 bases which encode at least three structural and six non-structural proteins. Based on sequence homology, the structural proteins have been functionally assigned as one single core protein and two envelope proteins: E1 and E2. The E1 protein consists of 192 amino acids and contains 5 to 6 N-glycosylation sites, depending on the HCV genotype. The E2 protein consists of 363 to 370 amino acids containing 9 to 11 N-glycosylation sites, depending on the HCV genotype (for review see Major and Feinstone, 1997; Maertens and Stuyver, 1997). The E1 protein contains various variable domains, while the E2 protein contains two hypervariable domains, of which the major domain is located at the N-terminus of the protein (Maertens and Stuyver, 1997). The envelope proteins have been produced by recombinant techniques in *Escherichia coli*, insect cells, yeast cells and mammalian cells. The usage of an expression system in higher eukaryotes and especially in mammalian cell culture leads to envelope proteins of superior quality, i.e. they are effectively recognised by antibodies in patient samples as described in PCT/EP 95/03031 to Maertens et al.

Currently, the detection of HCV in cells or tissues relies mainly on the demonstration of viral RNA. However, RNA detection in cells or tissues is a cumbersome technique which either involves the extraction of RNA followed by reverse transcription and nested PCR or includes in situ RT-PCR and hybridisation. Since these techniques are also prone to false positive reactivity, viral RNA detection is exclusively performed on serum samples. Reliable methods for the detection of viral protein antigens in serum and tissue samples are still lacking.

The replication sites of HCV have not yet been fully elucidated. It is generally accepted that the virus replicates in hepatocytes, but replication in other tissues, such as lymphoid tissues, is still highly debated. Hence, a reliable method for the detection of viral proteins or the virus itself in cells may solve this issue.

The detection of viral proteins in cells has been hampered by the lack of antibodies which specifically bind to viral proteins and which are able to specifically recognise the natural HCV protein antigens (i.e. antigens as expressed by the host following infection with HCV). As a consequence, to date only few studies relate to demonstrating the presence of viral HCV proteins in host cells (for review see Guido and Thung, 1996). Moreover, host-derived antibodies have been used in many of these studies. Preparations containing host-derived antibodies, however, cannot be reproduced easily and these preparations may be contaminated by autoimmune antibodies as well as by antibodies against other known or even unknown agents. In contrast, it is known that antibodies produced in animals upon immunisation with recombinant antigens will yield antibodies with the desired specificity. In order to have reproducible quality, monoclonal antibodies are preferred as well. In addition, the envelope proteins of HCV need to be produced by a mammalian expression system to yield good quality antigens. Currently, this expression condition goes together with incomprehensible problems. Therefore, only few monoclonal antibodies have been described which could be used to detect HCV envelope antigens in tissue specimens of patients. These antibodies were directed against the N-terminal region of E1, amino acids (aa) 192–226, (Hiramatsu et al., 1992, Kaito et al., 1994) or the C-terminal domain of E2, aa 451–715 (Sansonno et al., 1997a, 1997b). However, from these publications and from the reviews by Guido and Thung (1996), and Liang (1996) it is evident that there is still an existing need for well-characterised antibodies allowing efficient and routine detection of natural HCV protein antigens in serum and tissue samples. This need was recently confirmed by a study by Dries and co-workers (1999). Dries' group proved that 61% of HCV antibody positive and serum RNA negative individuals were carriers of HCV as HCV RNA could be detected in liver biopsy samples but only one third of these cases could be detected by immunohistochemistry using a panel of antibodies. Thus, routine detection of HCV antigen in liver biopsies still lacks sensitivity. Also the detection of viral antigens in body fluids such as serum or plasma is hampered by the same problem. Up to date only one single technique has been described allowing detection of core antigen in these fluids. However, in order to detect the core protein, the technique requires a complete denaturation of the core protein present in the sample using sodium hydroxide (Kashiwakutna et al., 1996).

Taken together, the identification of new specific HCV epitopes which are accessible for antibodies and which allow antigen detection in tissue or body fluid samples is therefore urgently needed. The HCV envelope proteins are putative candidate targets to find such epitopes, since these proteins should be present in all biological samples: in fluids, on the membrane of the virus, and in cells from the earliest event of infection (i.e. viral entry) throughout the complete replication cycle. However, these envelope proteins are highly variable so antibodies with a high cross-reactivity towards the different genotypes of HCV are needed. Thus, identification of such epitopes and the search for antibodies with high cross-reactivity towards the sequence variation of HCV is a challenging undertaking.

The present application relates to specific monoclonal antibodies, directed against particular epitopes in the envelope proteins of HCV, which are able to detect HCV antigen in tissue specimens of patients. In total two such epitopes, and corresponding antibodies, were found: one in the C-terminal region (aa 227–383) of the envelope protein E1 and one in the N-terminal hypervariable region (HVR) of E2 (aa 384–450). Although the latter region, and more specifically the region 395–415, is considered to be hypervariable, we characterised, to our surprise, an antibody which reacts with various known sequences of the HVR of E2.

AIMS OF THE INVENTION

It is clear from the literature that there is an urgent need to develop reliable diagnostic methods, reliable vaccines and effective therapeutic agents for HCV. Also sensitive and specific screening methods of HCV-contaminated blood-products and improved methods to culture HCV are needed. New antibodies able to detect the virus in animal—or in vitro models, or in its natural host, may help in designing efficient diagnostic tools and therapeutic agents. In this regard, the present invention is based on the surprising finding of monoclonal antibodies directed against either E1 or E2-HVR which can be used for the detection of HCV antigens in various tissues or cells. These tissues include the liver but also cells derived from blood samples. Therefore, the present invention aims at providing and using an antibody specifically binding to HCV envelope protein region aa 227–450, which covers the main part (C-terminal) of the E1 protein. and the N-terminal region of the E2 protein. These antibodies allow detection of natural HCV protein antigens, and can be used for the preparation of a natural HCV protein antigen detection kit. Notably, the complete E1 protein corresponds to aa 192–383, while the complete E2 protein corresponds to aa 384–747 (see: Major and Feinstone, 1997; Maertens and Stuyver, 1997).

More specifically, the present invention aims at providing and using an antibody as defined above which specifically binds to at least one of the following epitopes:

aa 307–326 of HCV E1 protein (SEQ ID 30)

aa 395–415 of HCV E2 protein (SEQ ID 31).

Moreover, the present invention aims at providing and using an antibody as defined above which is a monoclonal antibody. In this regard, the present invention aims at providing and using a monoclonal antibody secreted by the hybridoma line with ECACC deposit having the accession number 98031215 of 98031214, which were deposited with the European Collection of Cell Cultures, Center for Applied Microbiology & Research, Salisbury, Wiltshire SP4 OJG, UK, under conditions of the Budapest Treaty, on Mar. 12, 1998.

It should be clear that the present invention also aims at providing and using any functionally equivalent variant or fragment of any antibody as defined above, as well as mutant forms thereof, or molecules exhibiting similar functional binding reactivities with SEQ ID 30 and 31, such as sequences obtained from phage—or other libraries.

In addition, the present invention aims at providing and using a hybridoma cell line secreting a monoclonal antibody which specifically binds to HCV E1 protein (aa 227–383) or HCV E2 N-terminal hypervariable region (aa 384–450) and which allows the detection of natural HCV protein antigens, and can be used for the preparation of a natural HCV protein antigen detection kit More specifically, the present invention aims at providing and using the hybridoma cell line corresponding to the ECACC deposit having accession number 98031215 or 98031214.

Furthermore, the present invention also aims at providing a method for the detection of natural HCV protein antigens comprising:

contacting a test sample which may contain HCV protein antigens with an antibody as defined above or with a functionally equivalent variant or fragment of said antibody, to form an antibody-antigen complex, and determining said antigen-antibody complex with an appropriate marker.

More specifically, the present invention aims at providing a method as defined above wherein said test sample comprises human cells, such as peripheral blood cells, or human tissues, such as liver tissue.

Finally, the present invention aims at providing an assay kit for the detection of natural HCV protein antigens comprising:

an antibody as defined above, or, a functionally equivalent variant or fragment of said antibody, and appropriate markers which allow to determine the complexes formed between HCV protein antigens in a test sample with said antibody or a functionally equivalent variant or fragment of said antibody.

All the aims of the present invention are considered to have been met by the embodiments as set out below.

BRIEF DESCRIPTION OF TABLES AND DRAWINGS

Table 1 provides the peptide sequences of all peptides mentioned in this application.

Table 2 shows the cross-reactivity of IGH 222 towards various sequences of the hyper-variable domain in E2. All peptides were biotinylated, bound to streptavidin-coated microtiterplates and allowed to react with IGH 222.

FIG. 1 shows staining of E2 antigen, revealed by the monoclonal antibody IGH 222, on a liver biopsy of an HCV patient. Immunohistochemistry was performed on 4 $\mu$m thick cryostat sections of fresh frozen materials (the liver biopsy was snap-frozen in liquid nitrogen-cooled isopentane and stored at −70° C. until use) using a three step indirect immuno-peroxidase procedure. Sections were incubated overnight at 4° C. with monoclonal antibody IGH 222 (purified IgG$_1$: 10 ng/$\mu$l). The secondary and tertiary antibodies consisted of peroxidase-conjugated rabbit anti-mouse and peroxidase-conjugated swine anti-rabbit IgG, respectively (both obtained from Dakopatts, Copenhagen, Denmark; working dilution 1/50 and 1/100, respectively). Each incubation was performed 30 minutes at room temperature and followed by a wash in three changes of phosphate buffered saline, pH 7.2. The reaction product was developed by incubation for 15 minutes in 100 mM acetate buffer (pH 5.2), containing 0.05% 3-amino-9-ethyl-carbazole and 0.01% $H_2O_2$, resulting in bright red staining of immuno-reactive sites. The sections were counterstained with haemotoxylin. Controls (not shown) consisted of irrelevant monoclonal antibodies of similar isotype as the primary antibody, or of chromogen alone: these controls were consistently negative. The photograph shows a 25× magnification. The darkest staining reveals the presence of HCV antigen in hepatocytes only (see arrows).

Figure 2A:
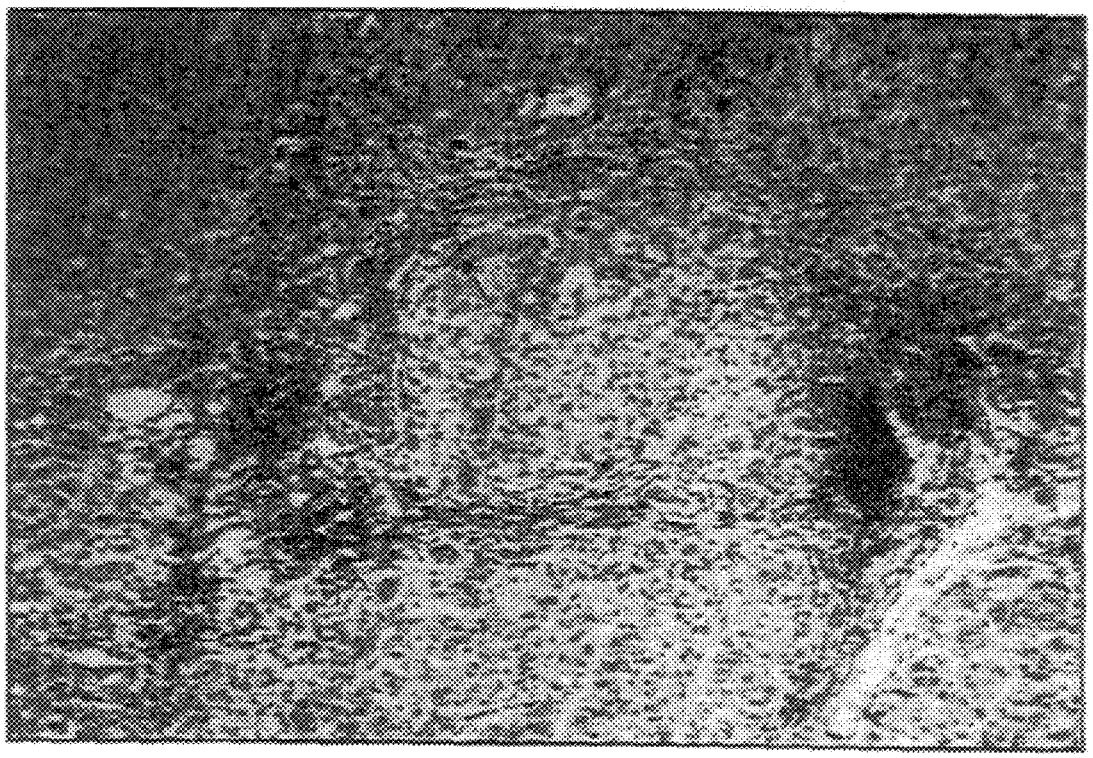

FIG. 2A shows staining of E1 antigen, revealed by the monoclonal antibody IGH 207, on a liver biopsy of an HCV patient. The procedure followed is identical to the one described in figure 1, except for the concentration of the monoclonal antibody which was 30 ng/$\mu$l. The photograph shows a 10× magnification on which the staining of the cells in the lymphocyte infiltrates is dominant. The darkest staining reveals the presence of HCV antigen in hepatocytes (see arrow) and in infiltrating lymphocytes (see double arrow).

Figure 2B:
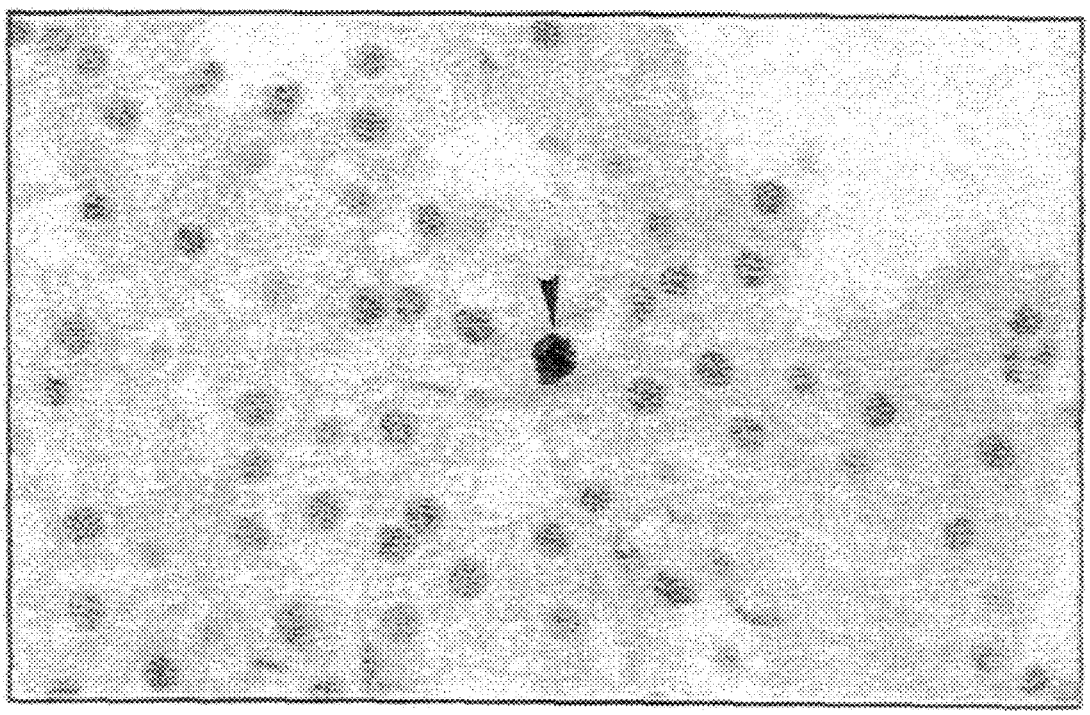

FIG. 2B shows staining of E1 antigen, revealed by the monoclonal antibody IGH 210, on a liver biopsy of an HCV patient. The liver biopsy was fixed with formaldehyde and embedded in paraffin. Sections were pretreated by heat (microwave method) and by protease digestion. The concentration of the antibody was 6 ng/µl. The photograph shows a clearly stained isolated mononuclear cell (arrow) in a field of hepatocytes, which do not stain with this monoclonal.

Figure 3:
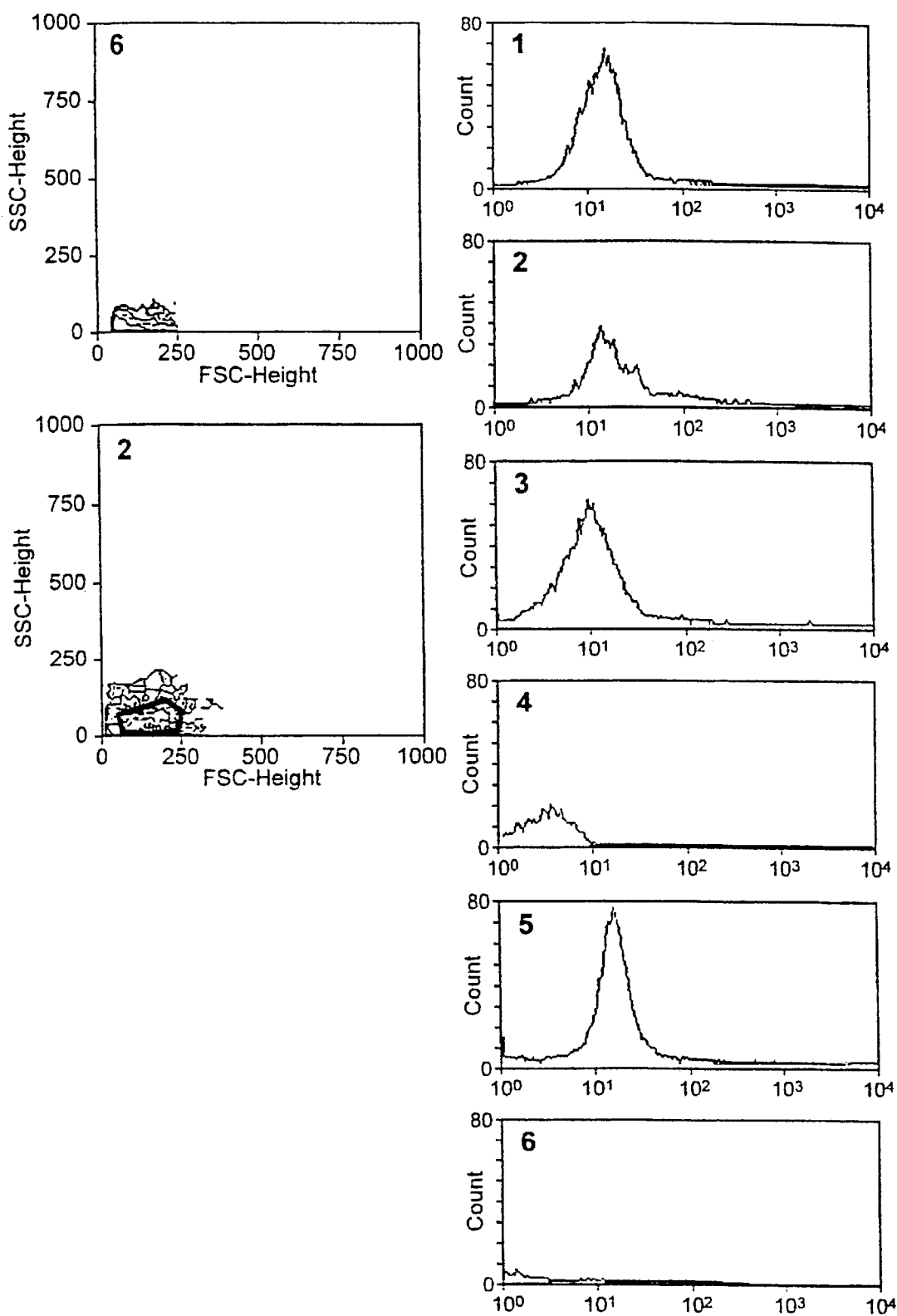

FIG. 3 shows staining, revealed by the monoclonal antibody IGH 207, of intracellular E1 antigen in peripheral blood mononuclear cells. Peripheral white blood cells (0.5× $10^6$) were suspended in 200 µl PBS-0.1% saponin, 2 µg of IGH 207 was added and allowed to react for 25 minutes at 4° C. The cells are washed three times with 3 ml PBS-0.1% saponin and three times with PBS-0.2% $NaN_3$. Finally cells are resuspended in 250 µl of PBS-0.2% $NaN_3$ and analysed by flow cytometry. After gating on the mononuclear cell fraction (right column), the fluorescence was plotted (left column). Samples 1–5 are derived from HCV chronic carriers while sample 6 is derived from a healthy blood carrier. The left column shows two examples of the gating on the mononuclear cell fraction (samples 2 and 6), while the right column shows the fluorescence found in these mononuclear cells. While the control sample shows no staining at all with this monoclonal antibody, there is a marked positive signal in all HCV patients, except for patient 4 for whom a weaker signal was obtained.

Figure 4:
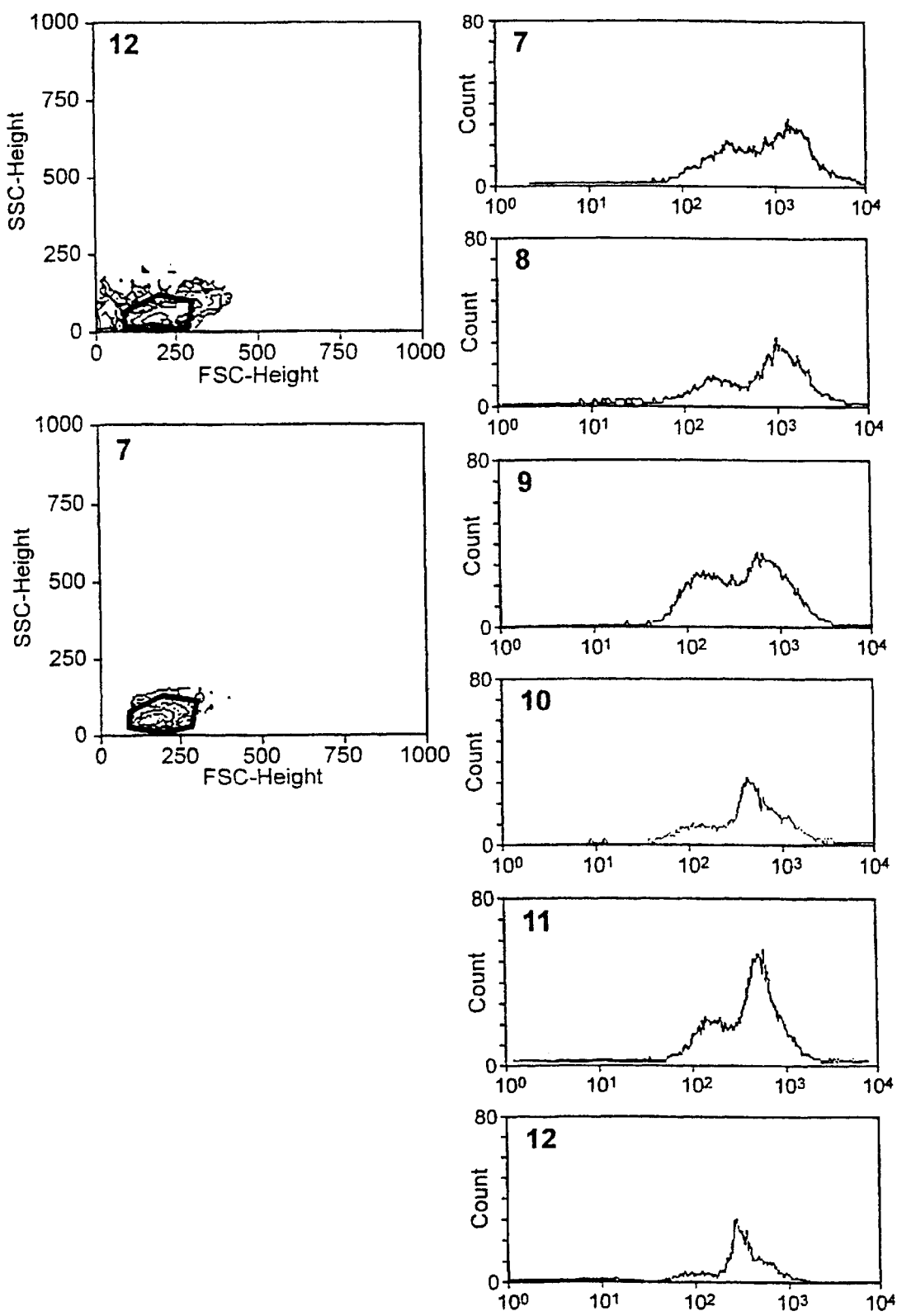

FIG. 4 shows staining, revealed by the monoclonal antibody IGH201, of intracellular E1 antigen in peripheral blood mononuclear cells. The technique was similar as described for FIG. 3. Samples 7–11 are derived from HCV chronic carriers while sample 12 is derived from a healthy blood carrier. The left column shows two examples of the gating on the mononuclear cell fraction (samples 7 and 12), while the right column shows the fluorescence found in these mononuclear cells. Although the control sample reveals a higher background staining, the reaction in the patient samples can be easily discriminated based on the two populations which can be detected: a population with a similar staining as in the control and a second population with high intensity staining, not seen in the control.

DETAILED DESCRIPTION OF THE INVENTION

The invention described herein draws on previously published work and pending patent applications. By way of example, such work consists of scientific papers, patents or pending patent applications. All these publications and applications, cited previously or below are hereby incorporated by reference.

It is clear that the detection of viral proteins has been hampered by the lack of antibodies which specifically bind to viral proteins and which are able to recognise the natural HCV protein antigens (i.e. protein antigens as expressed by the host following infection with HCV). The present invention is based on the finding of two new epitopes on the HCV envelope proteins which allow routine detection of natural HCV protein antigens, by means of antibodies directed against these epitopes, in biological samples derived from the host. Thus, the present invention relates to the use of antibodies specifically binding to the C-terminal region of HCV E1 protein (aa 227–383) or the N-terminal region of the HCV E-2 protein (aa 384–450) for the preparation of a natural HCV protein antigen detection kit. The term "antibodies specifically binding to the C-terminal region of the HCV E1 protein (aa 227–383) or the N-terminal region of the HCV E2 protein (aa 384–450)" refers to any polyclonal or monoclonal antibody binding to an hepatitis C viral particle or any molecule derived from said viral particle, more particularly to the C-terminal region of the E1 protein and the N-terminal region of the E2 protein. The "envelope region" of the HCV viruses, and thus "the C-terminal region of the HCV E1 protein (aa 227–383) or the N-terminal region of the HCV E2 protein (aa 384–450)" are well-known regions by a person skilled in the art (Wengler, 1991; Major and Feinstone, 1997; Maertens and Stuyver, 1997).

The term "bind" indicates that the antibodies of the present invention are physically connected to HCV proteins. In particular, that the antibodies specifically bind to the HCV envelope proteins, implying that there is substantially no cross-reaction with other components of HCV or other proteins. Binding of the antibody to HCV proteins can be demonstrated by any method or assay known in the art, such as binding-, ELISA-, and RIA-type of assays or competition assays (e.g. see Current protocols in immunology). It should be clear that the region of an HCV envelope protein which binds to an antibody need not to be composed of a contiguous sequence.

The term "monoclonal antibody" used herein refers to an antibody composition having a homogeneous antibody population. The term is not limiting regarding the species or source of the antibody, nor is it intended to be limited by the manner in which it is made. In addition, the term "antibody" also refers to humanised antibodies in which at least a portion of the framework regions of an immunoglobulin are derived from human immunoglobulin sequences and single chain antibodies as described in U.S. Pat. No. 4,946,778 and to fragments of antibodies such as $F_{ab}$, $F_{(ab)2}$, $F_v$, and other fragments which retain the antigen binding function and specificity of the parent antibody. Also included in the term "antibody" are diabodies, triabodies and tetravalent antibodies, as described in EP application N° 97870092.0 to Lorré et al., which retain the antigen binding function and specificity of the parent antibody. It should be clear that the antibodies as described in the present invention could be used in a method for the detection of natural HCV protein antigens.

The term "test sample" refers to any sample obtained from a host, such as serum, plasma, saliva, mucus, spinal cord fluid. or biopsies. In this regard, the terms "test sample" and "biological sample" are used interchangeable herein. The term "biopsy" particularly refers to a sample comprising cells, in particular human cells. Moreover, the latter term refers also to a sample derived from liquid tissue, such as peripheral blood cells, or from solid tissue, such as liver tissue. In case antigen detection is performed on a biopsy, the term "in situ detection" is used.

The term "natural HCV protein antigen detection kit" refers to a kit for the detection of any HCV protein antigen, preferentially to the detection of the C-terminal region of the HCV E1 protein (aa 227–383) or the N-terminal region of the HCV E2 protein (aa 384–450) in their natural or original position, preferentially the antigens as present in a test sample, by any method known to the man skilled in the art. In other words, the latter term refers to the visualisation of the presence of the C-terminal region of HCV E1 (aa 227–383) protein or the N-terminal region of the HCV E2 protein (aa 384–450) in, or on, their natural host cell or tissue by binding of the antibodies of the present invention. The detection kit comprises the following components:

(i) when appropriate a means for isolating a test sample, (ii) possibly a solution to permeabilise cells, (iii) an antibody as described herein, or a functionally equivalent variant or fragment thereof, (iv) possibly secondary and possibly tertiary antibodies, (v) possibly incubation and/or washing buffers, (vi) possibly a staining solution.

Preferentially, said kit is used for the in situ detection of HCV envelope proteins.

The natural host cell or tissue can be any host cell or tissue derived from any host species. In particular, the natural host cell refers to peripheral blood cells and the natural tissue refers to liver tissue (see also Examples section of the present application). The natural host refers, in particular, to humans but may also refer to non-human primates or other mammals.

More specifically, the present invention relates to antibodies, which specifically bind to at least one of the following epitopes: aa 307–326 of HCV E1 protein and aa 395–415 of HCV E2 protein. The latter antibodies are secreted by hybridomas deposited at the European Collection of Cell Cultures (ECACC), Center for Applied Microbiology & Research, Salisbury, Wiltshire SP4 OJG, U.K. (Tel: +44 1980 612512; fax: +44 1980 611315) on Mar. 13, 1998, which have been assigned the following accession numbers: 98031215 for hybridoma 17H10F4D10 secreting, mAb IGH 222, which binds epitope aa 395–415 (SEQ ID 31), and, 98031214 for hybridoma 14H11B2 secreting mAb IGH 207, which binds epitope aa 307–326 (SEQ ID 30). In this regard, it should be clear that antibodies that bind to parts of said epitopes are also part of the present invention. For example, antibodies binding to the following epitopes are hereby also included:

aa307–311, aa308–312, aa309–313, aa310–314, aa311–315, aa312–316, aa312–317, aa313–318, aa314–319, aa315–320, aa316–321, aa317–322, aa318–323, aa319–324, aa320–325, aa321–326, aa307–312, aa308–313, aa309–314, aa310–315, aa311–316, aa312–317, aa313–318, aa314–319, aa315–320, aa316–321, aa317–322, aa318–323, aa319–324, aa320–325, aa321–326, aa307–313, aa308–314, aa309–315, aa310–316, aa311–317, aa312–318, aa313–319, aa314–320, aa315–321, aa316–322, aa317–323, aa318–324, aa319–325, aa320–326, aa307–314, aa308–315, aa309–316, aa310–317, aa311–318, aa312–319, aa313–320, aa314–321, aa315–322, aa316–323, aa317–324, aa318–325, aa319–326, aa307–315, aa308–316, aa309–317, aa310–318, aa311–319, aa312–320, aa313–321, aa314–322, aa315–323, aa316–324, aa317–325, aa318–326, aa307–316, aa308–317, aa309–318, aa310–319, aa311–320, aa312–321, aa313–322, aa314–323, aa315–324, aa316–324, aa317–326, aa307–317, aa308–318, aa309–319, aa310–320, aa311–321, aa312–322, aa313–323, aa314–324, aa315–325, aa316–326, aa307–318, aa308–319, aa309–320, aa310–321, aa311–322, aa312–323, aa313–324, aa314–325, aa315–326, aa307–319, aa308–320, aa309–321, aa310–322, aa311–323, aa312–324, aa313–325, aa314–326, aa307–320, aa308–321, aa309–322, aa310–323, aa311–324, aa312–325, aa313–326, aa307–321, aa308–322, aa309–323, aa310–324, aa311–325, aa312–326, aa307–322, aa308–323, aa309–324, aa310–325, aa311–326, aa307–323, aa308–324, aa309–325, aa310–326, aa307–324, aa308–325, aa309–326, aa307–325, aa308–326, and, aa395–399, aa396–400, aa397–401, aa398–402, aa399–403, aa400–404, aa401–405, aa402–406, aa403–407, aa404–408, aa405–409, aa406–410, aa407–411, aa408–412, aa409–413, aa410–414, aa411–415, aa395–400, aa396–401, aa397–402, aa398–403, aa399–404, aa400–405, aa401–406, aa402–407, aa403–408, aa404–409, aa405–410, aa406–411, aa407–412, aa408–413, aa409–414, aa410–415, aa395–401, aa396–402 aa397–403, aa398–404, aa399–405, aa400–406, aa401–407, aa402–408, aa403–409, aa404–410, aa405–411, aa406–412, aa407–413, aa408–414, aa409–415, aa395–402, aa396–403, aa397–404, aa398–405, aa399–406, aa400–407, aa401–408, aa402–409, aa403–410, aa404–411, aa405–412, aa406–413, aa407–414, aa408–415, aa395–404, aa396–404, aa397–405, aa398–406, aa399–407, aa400–408, aa401–409, aa402–410, aa403–411, aa404–412, aa405–413, aa406–414, aa407–415, aa395–403, aa396–404, aa397–405, aa398–406, aa399–407, aa400–408, aa401–409, aa402–410, aa403–411, aa404–412, aa405–413, aa406–414, aa407–415, aa395–404, aa396–405, aa397–406, aa398–407, aa399–408, aa400–409, aa401–410, aa402–411, aa403–412, aa404–413, aa405–414, aa406–415, aa395–405, aa396–406, aa397–407, aa398–408, aa399–409, aa400–410, aa401–411, aa402–412, aa403–413, aa404–414, aa405–415, aa395–406, aa396–407, aa397–408, aa398–409, aa399–410, aa400–411, aa401–412, aa402–413, aa403–414, aa404–415, aa395–407, aa396–408, aa397–409, aa398–410, aa399–411, aa400–412, aa401–413, aa402–414, aa403–415, aa395–408, aa396–409, aa397–410, aa398–411, aa399–412, aa400–413, aa401–414, aa402–415, aa395–409, aa396–410, aa397–411, aa398–412, aa399–413, aa400–414, aa401–415, aa395–410, aa396–411, aa397–412, aa398–413, aa399–414, aa400–415, aa395–411, aa396–412, aa397–413, aa398–414, aa399–415, aa395–412, aa396–413, aa397–414, aa398–415, aa395–413, aa396–414, aa397–415, aa395–414 and 396–415, The present invention also relates to functionally equivalent variants or fragments of the above-indicated antibodies. The term "functionally equivalent variants or fragments" refers to any variant or fragment known in the art of said antibodies which retain the antigen binding function and specificity of the parent antibody.

More specifically, the latter term refers to humanised antibodies and single chain antibodies as defined above and to fragments of antibodies such as $F_{ab}$, $F_{(ab)2}$, $F_v$, and the like. Also included are diabodies. triabodies and tetravalent antibodies, as described above, as well as mutant forms thereof or molecules exhibiting similar functional binding reactivities with SEQ ID 30 and 31, such as sequences obtained from phage- or other libraries as described by Ladner, 1995; Maclennan, 1995 and Cannon et al., 1996. Indeed, any peptide described by these authors, constrained or not, which allows the detection of natural HCV protein antigens is part of the present invention.

The present invention also relates to hybridoma cell lines secreting antibodies as defined above In this regard, it should be clear that the hybridoma technology for obtaining mAbs is well known to a person skilled in the art, e.g. essentially according to Kohler and Milstein (1975). It should also be clear that mapping the epitopes to which the mAbs specifically bind can be performed by any method known in the art such as the ones described in PCT/EP 97/07268 to Depla et al.

The present invention also relates to a method for the detection of natural HCV protein antigens comprising:

contacting a test sample which may contain HCV protein antigens with an antibody as defined above or with a functionally equivalent variant or fragment of said antibody, to form an antibody-antigen complex, and determining said antigen-antibody complex with an appropriate marker.

Preferentially, said method is used for the in situ detection of HCV envelope proteins.

The term "determining said antigen-antibody complex with an appropriate marker" refers to any method known in the art which detects, or visualises, the above-indicated antigen-antibody complexes, such as fluorescence flow cytometry, binding-, ELISA- and RIA-type assays or competition assays (see Examples section, Hertogs et al, 1993, and, WO 93/04084 to Mehta et al.). Similarly, the term "appropriate marker" refers to any marker known in the art such as the ones described in WO 93/04084 to Mehta et al. and Coligan et al., 1992 which visualises the above-indicated antigen-antibody complexes.

In this regard, the present invention also relates to an assay kit for the detection of natural HCV protein antigens comprising: an antibody as defined above, or, a functionally equivalent variant or fragment of said antibody, and appropriate markers which allow to determine the complexes formed between HCV protein antigens in a test sample with said antibody or a functionally equivalent variant or fragment of said antibody.

The present invention will now be illustrated by reference to the following examples that set forth particularly advantageous embodiments. However, it should be noted that these embodiments are merely illustrative and can not be construed as to restrict the invention in any way.

EXAMPLES

Example 1

Generation of Monoclonal Antibodies Against E1 and E2

Mice were immunised with truncated versions of E1 (aa 192–326) and E2 (aa 384–673), expressed by, recombinant vraccinia virus as described in PCT/EP 95/03031 to Maertens et al. After immunisation splenocytes of the mice were fused with a myeloma cell line. Resulting hybridomas secreting specific antibodies for E1 or E2 were selected by means of ELISA.

Example 2

Selection of Monoclonal Antibodies

A large series (25 in total, of which 14 in detail; the latter can be obtained from Innogenetics NV, Gent, Belgium) of monoclonals directed against E1 or E2 was evaluated for staining of native HCV antigen in liver biopsies of HCV patients and controls (see below). Staining was performed either on cryosections or on formadehyde fixed biopsies (for protocols. see figure legends). Only three monoclonal antibodies revealed a clear and specific staining. All other monoclonal antibodies either gave no or very weak staining, or showed non-specific staining,. Remarkably, two different antigen staining patterns were noticed. Monoclonal IGH 222, directed against E2, clearly stained hepatocytes (FIG. 1), while IGH 207 and IGH 210, directed against E1, stained lymphocytes infiltrating in the liver (FIGS. 2a and 2b). IGH 207 also stained hepatocytes, but to a weaker degree than IGH 222 (compare FIGS. 1 and 2a). This-staining pattern was confirmed on a series of biopsies of five different patients.

| Monoclonal | envelope | staining pattern |
|---|---|---|
| IGH 200 | E1 | negative |
| IGH 201 | E1 | weak |
| IGH 202 | E1 | negative |
| IGH 204 | E1 | weak |
| IGH 207 | E1 | strong positivity of lymphocytes, weaker positivity of hepatocytes |
| IGH 209 | E1 | negative |
| IGH 210 | E1 | positive on lymphocytes (only noted after formaldehyde fixation) |
| IGH 212 | E2 | weak |
| IGH 214 | E2 | negative |
| IGH 215 | E2 | negative |
| IGH 216 | E2 | negative |
| IGH 219 | E2 | negative |
| IGH 221 | E2 | negative |
| IGH 222 | E2 | strong positivity of hepatocytes |

Example 3

Identification of Monoclonal Antibodies Allowing Detection of Viral Envelope Antigen in Peripheral Blood Cells The finding that lymphocyte infiltrates in the liver can be stained for HCV envelope antigens prompted us to look also at peripheral blood mononuclear cells. In order to allow intracellular staining, peripheral blood cells were permeabilised with saponin, allowed thereafter to react with the monoclonal antibodies IGH 201 or 207 (directed against E1 and showing weak and strong positivity on the liver biopsies, respectively). Finally, reactivity was checked on a fluorescent cell sorter using secondary FITC-labelled antibodies. IGH 207, which stained already the lymphocyte infiltrates in the liver, showed a high specificity. With this monoclonal, almost no background staining was detected, and 4 out of 5 patients clearly stained positive (FIG. 3). The second monoclonal, IGH 201 (binding to SEQ ID 29; ECACC accession number: 98031216) which is also directed against E1, yields a higher background but intracellular E1 was detected in 5 out of 5 patients as can be deduced from the histograms presented in FIG. 4, which show a clear subpopulation of cells with a higher degree of fluorescence as compared to the control sample.

Example 4

Mapping of the Reactive Monoclonal Antibodies against E1 or E2

All 14 monoclonal antibodies were mapped to their respective epitopes using peptides scanning the E1 and E2 protein against which the antibodies were raised. These peptides were biotinylated, bound to streptavidin sensitized microtiterplates, and allowed to react with the monoclonal antibodies. As a positive control recombinant envelope proteins were checked.

For each monoclonal antibody reactivity could be assigned to a specific epitope region defined by two overlapping peptides .(for details on sequences see Table I).

| peptides | aa region | reactive monoclonals |
|---|---|---|
| V1V2 | 192–226 | IGH 201, 204, 202, 200 |
| V2V3 | 212–244 | IGH 201, 204, 202, 200 |
| V3V4 | 230–263 | |
| HR | 261–290 | |
| V5C4 | 288–327 | IGH 207, 210, 209 |
| C4V6 | 307–340 | IGH 207, 210, 209 |
| recombinant | 192–326 | IGH 201, 207, 210, 204, 202, 200, 209 |
| HVRI | 384–415 | IGH 222, 215 |
| HVR1/C1a | 395–428 | IGH 222, 215 |
| C1a | 413–447 | |
| C1b | 430–467 | |
| HVRII | 460–487 | IGH 212, 214, 221 |
| C2a | 480–513 | IGH 219, 216 |
| C2b | 500–530 | |
| V3-C3 | 523–566 | |
| V4 | 561–590 | |

-continued

| peptides | aa region | reactive monoclonals |
| --- | --- | --- |
| C4a | 578–627 | |
| C4b | 621–648 | |
| C4c | 641–673 | |
| recombinant | 384–673 | IGH 222, 215.212, 214, 221, 219, 216 |

The epitope for IGH 201 can be defined as the region 212–226 (SEQ ID9), for IGH 207 and IGH 210 this is 307–326 (SEQ ID 30) and for IGH 222 this is 395–415 (SEQ ID 31). The amino acid region of IGH 201 is a rather variable region of the E1 protein of HCV and has already been previously reported in relation to in situ detection of HCV (Hiramatsu et al., 1992, Kaito et al., 1994). However, from our studies it is clear that antibodies directed against this epitope are less suitable for in situ detection of HCV as the liver biopsy staining with this antibody was negative and the staining on peripheral blood lymphocytes showed considerable background. In contrast, IGH 207 and IGH 210 recognise a completely conserved region of E1 (Maertens and Stuyver, 1997). The monoclonal IGH 222 recognises a region of E2, which is part of the N-terminal hypervariable domain of E2, and proved to be very suitable for efficient in situ detection of HCV.

Example 5

Determination of Cross-reactivity on Variable Epitopes

Using an extended series of peptides derived from various sequences of the N-terminal hypervariable epitope of E2, IGH 222 was further characterised. Table 2 shows a summary of these experiments. From this table it can be concluded that this monoclonal reacts with several sequences, but fails to react with some others. Knowing this epitope is sufficient for the man skilled in the art to raise additional antibodies against this epitope with a better reactivity towards other sequences which are not recognised by IGH 222. Such sequences are by way of example the peptides with # 490, 940, 884, 484 and 494 but other sequences in the region between aa 395–415 may be found against which IGH 222 may fail to react.

From these examples it is clear that the epitopes recognised by the monoclonal antibodies IGH 201, 207, 210 and 222 are readily accessible for binding antibodies and allow detection of the antigen in liver biopsies and peripheral blood cells. The properties of the monoclonal antibodies IGH 201, 207, 210 and 222 are rather unique, since other monoclonals directed against the same epitopes resulted in high background and absence of specific staining. For example, the monoclonal antibodies IGH 207, 209 and 210 all recognise the same epitope, however, IGH 209 is not able to stain E1 antigen in any cell type, while IGH 210 only stains lymphocytes and IGH 207 stains both lymphocytes and hepatocytes. With the instant invention, it should be feasible for the man skilled in the art to produce large series of antibodies (either polyclonal or monoclonal of nature, in various species), that can be used for detection of natural HCV protein antigens.

The need to produce a series of antibodies against a given epitope reflects the fact that the behavior of an antibody is not exclusively determined by the epitope recognised but also by secondary properties such as affinity and avidity for the epitope, solubility, isotype, and the species in which it is generated. For each application an antibody with different secondary properties may be required. Thus, the production of such large series of antibodies will allow to identify some of them as having similar properties as IGH 201, 207, 210 and 222 i.e. to be able to reveal the presence of HCV envelope protein in biological samples of the host. Indeed, the knowledge that these epitopes are clearly accessible on the HCV envelope proteins, as expressed in the host, provides the necessary information to develop assays to detect these antigens not only in situ as presented here but also in solution (eg in plasma or serum). The monoclonal antibodies IGH 201, 207, 210 or 222, or others developed against the same epitope but with optimal characteristics for detection of soluble antigen, possibly in combination with others, could also be used to develop such an assay.

LIST OF REFERENCES

Cannon, E., Ladner R., and McCoy D. Phage-display technology. IVD Technology 1996, Nov/Dec.

Current protocols in immunology. Eds Coligan J., Kruisbeek A., Margulis D., Shevach E., and Strober W. Wiley Interscience, 1992.

Dries V., Von Both I., Müller M., Gerken G., Schirmacher P., Odenthal M., Bartenschlager R., Drebber U., Meyer Zum Büschenfelde K.-H. And Dienes H. P. Detection of Hepatitis C virus in paraffin-embedded liver biopsies of patients negative for viral RNA in serum. Hepatology 1999: 29: 223–229.

Guido M and Thung S. The value of identifying hepatitis C virus in liver pathology specimens. Hepatology 1996: 23: 376–379.

Hiramatsu N., Hayashi N., Haruna Y., Kasahara A., Fusamoto H., Mori C., Fuke I., Okayama H. and Kamada T. lmmunohistochemical detection of hepatitis C virus-infected hepatocytes in chronic liver disease with monoclonal antibodies to core, envelope and NS3 regions of the hepatitis C virus genome. Hepatology 1992: 16: 306–311.

Kaito M., Watanabe S., Tsukiyama-Kohara K., Yamaguchi K., Kobayashi Y., Konishi M., Yokoi M., Ishida S., Suzuki S. and Kohara M. Hepatitis C virus particle detected by immunoelectron microscopic study. J. Gen. Virol. 1994: 75: 1755–1760.

Kashiwakuma T., Hasegawa A., Kajita T., Takata A., Mor H., Ohta Y., Tanaka E., Kiyosawa K., Tanaka T., Tanaka S., Hattori N. And Kohara M. Detection of hepatitis C virus specific core protein in serum of patients by a sensitive fluorescence enzyme immunoassay. J. Immunol. Meth. 1996: 190: 79–89.

Kohler and Milstein, (1975) Continuous cultures of fused cells secreting antibody of predefined specificity. Nature 256: 495.

Lang, T. J. (1996) Hepatology elsewhere 23: 376–379.

Ladner, R. Constrained peptides as binding entities. Tibtech 1995, 13:426–430.

Maclennan J. Engineering microprotein ligands for large-scale affinity purification. Biotechnology 1995, 13:1181–1183.

Maertens G. and Stuyver L. Genotypes and genetic variation of hepatitis C virus. In: The molecular medicine of viral hepatitis. Ed: Harrison T. J. and Zuckerman A. J. 1997

Major M. E. and Feinstone S. M. The molecular virology of hepatitis C. Hepatology 1997: 25: 1527–1538.

Sansonno D., Cornacchiulo V., Racanelli V. and Dammacco F. In situ simultaneous detection of hepatitis C virus RNA and hepatitis C virus-related antigens in hepatocellular carcinoma. Cancer 1997: 80: 22–33.

Sansonno D., Gesualdo L., Manno C., Schena F. and Dammacco F. Hepatitis C virus-related proteins in kidney tissue from hepatitis C virus-infected patients with cryoglobulinemic membranoproliferative glomerulonephritis. Hepatology 1997: 25: 1237–1244.

TABLE 1

| E1 peptides | Genotype | name | # | aa |
|---|---|---|---|---|
| YQVRNSTGLYHVTNDCPNSSIVYEAADAILHTPGC | 1a | V1V2 | 1071 | 192–226 |
| YEVRNVSGIYHVTNDCSNSSIVYEAADMIMHTPGC | 1b | V1V2 | 888 | 192–226 |
| VEVKNNSNSYMATNDCSNSSIIWQLEGAVLHTPGC | 2a | V1V2 | 1019 | 192–226 |
| VEVKNTSTSYMVTNDCSNSSIVWQLEGAVLHTPGC | 2c | V1V2 | 1074 | 192–226 |
| LEWRNTSGLYVLTNDCSNSSIVYEADDVILHTPGC | 3 | V1V2 | 1008 | 192–226 |
| INYRNVSGIYHVTNDCPNSSIVYEADHHILHLPGC | 4 | V1V2 | 1075 | 192–226 |
| VPYRNASGIYHITNDCPNSSIVYEADNLILHAPGC | 5 | V1V2 | 1084 | 192–226 |
| LTYGNSSGLYHLTNDCSNSSIVLEADAMILHLPGC | 6 | V1V2 | 1023/1085 | 192–226 |
| LNYANKSGLYHLTNDCPNSSIVYEANGMILHLPG | 7 | V1V2 | 1334 | 192–225 |
| IQVKNASGIYHLTNDCSNSSIVFEAETMILHLFGC | 9 | V1V2 | 1333 | 192–226 |
| LEYRNASGLYMVTNDCSNGSIVYEAGDIILHLPGC | 10 | V1V2 | 1332 | 192–226 |
| IVYEAADMIMHTPGCVPCVRENNSSRCWV | 1b | V2V3 | 1036 | 212–244 |
| VRENNSSRCWVALTPTLAARNASVPTTTIRTUIVD | 1b | V3V4 | 1022 | 230–263 |
| HVDLLVGAAAFCSAMYVGDLCGSVFLVSQL | 1b | HR | 1150 | 261–290 |
| SQLFTISPRRHETVQDCNCSIYPGHITGHRMAWDMMMNWS | 1b | V5C4 | 1176 | 288–327 |
| SIYPGHITGHRMAWDMMMNWSPTTALVVSQLLRI | 1b | C4V6 | 1039 | 307–340 |
| HTRVSGGAAASNTRGLVSLFSPGSAQKIQLVN | 1b | HVR I | 1139 | 384–415 |
| NTRGLVSLFSPGSAQKIQLVNTNGSWHINRTALN | 1b | HVR I/C1a | 1113 | 395–428 |
| LVNTNGSWHINRTALNCNDSLQTGFFAALFYKHKF | 1b | C1a | 1149 | 413–447 |
| NDSLQTGFFAALFYKHKFNSSGCPERLASCRSIDKFAQ | 1b | C1b | 1148 | 430–467 |
| RSIDKFAQGWGPLTYTEPNSSDQRPYCW | 1b | HVR II | 1020 | 460–487 |
| SDQRPYCWHYAPRPCGIVPASQVCGPVYCFTPSP | 1b | C2a | 1147 | 480–513 |
| SQVCGPVYCFTPSPVVVGTTTDRFGVPTYNWG | 1b | C2b | 1143 | 500–530 |
| GVPTYNWGANDSDVLILNNTRPPRGNWFGCTWMNGTGFTKTCGG | 1b | V3–C3 | 1178 | 523–566 |
| TKTCGGPPCNIGGAGNNTLTCPTDCFRKHP | 1b | V4 | 1142 | 561–590 |
| TDCFRKHPEATYARCGSGPWLTPRCMVHYPYRLWHYPCTVNFTIF | 1b | C4a | 16 | 583–627 |
| TVNFTIFKVRMYVGGVEHRFEAACNWTR | 1b | C4b | 1141 | 621–648 |
| EAACNWTRGERCDLEDRDRSELSPLLLSTTLWQ | 1b | C4c | 1140 | 641–673 |
| KTTNRLVSMFASGPKQNVHLINT | — | HVR I | 485 | 394–416 |
| HTTSTLASLFSPGASQRIQLVNT | — | HVR I | 492 | 395–416 |
| HVTCTLTSLFRPGASQKIQLVNT | — | HVR I | 489 | 394–416 |
| ARNARTLTGMFSLGARQKIQLINT | — | HVR I | 520 | 394–416 |
| SDTRGLVSLFSPGSAQKIQLVNT | — | HVR I | 886 | 394–416 |
| SSTQSLVSWLSQGPSQKIQLVNT | — | HVR I | 494 | 394–416 |
| HTMTGIVRFFAPGPKQNVHLINT | — | HVR I | 484 | 394–416 |
| RAMSGLVSLFTPGAKQNIQLINT | — | HVR I | 884 | 394–416 |
| HVTGTLTSLFRPGASQKIQLVNT | — | HVR I | 940 | 394–416 |

TABLE 2

| Sequence | # | aa region | Recognition by IGH 222 |
|---|---|---|---|
| HTRVSGGAAASNTRGLVSLFSPGSAQKIQLVN | 1139 | 384–415 | + |
| KTTNRLVSMFASGPKQNVHLINT | 485 | 394–416 | + |
| HTTSTLASLFSPGASQRIQLVNT | 492 | 395–416 | + |
| AHNARTLTGMFSLGARQKIQLINT | 520 | 394–416 | + |
| SDTRGLVSLFSPGSAQKIQLVNT | 886 | 394–416 | + |
| SSTQSLVSWLSQGPSQKIQLVNT | 494 | 394–416 | − |
| HTMTGIVRFFAPGPKQNVHLINT | 484 | 394–416 | − |
| RAMSGLVSLFTPGAKQNIQLINT | 884 | 394–416 | − |
| HVTGTLTSLFRPGASQKIQLVNT | 940 | 394–416 | − |
| RTTQGLVSLFSRGAKQDIQLINT | 490 | 394–416 | − | non-conservative mutations in the peptides not reacting with IGH 222 are shown in bold

What is claimed is:

1. A method for detection of natural HCV protein antigens comprising contacting a test sample which is suspected of containing HCV protein antigens with an antibody secreted by the hybridoma cell line of ECACC deposit having accession number 98031214, or a functionally equivalent varient or fragment thereof, to form an antibody-antigen complex, and determining the presence of said antigen-antibody complex with an appropriate marker.

2. The monoclonal antibody secreted by the hybridoma cell line of ECACC deposit having accession number 98031214.

3. The functionally equivalent variant or fragment of the antibody according to claim 2.

4. The hybridoma cell line of ECACC deposit having accession number 98031214.

5. The method according to claim 1, wherein said test sample comprises human cells or tissues.

6. The method according to claim 5, wherein said human cells are peripheral blood cells.

7. The method according to claim 5, wherein said human tissue is liver tissue.

8. An assay kit for the detection of natural HCV protein antigens comprising:

an antibody according to claims 2 or 3, and optionally, appropriate markers which allow the determination of the complexes formed between HCV protein antigens in a sample with said antibody or a functionally equivalent varient or fragment of said antibody.

* * * * *

UNITED STATES PATENT AND TRADEMARK OFFICE
CERTIFICATE OF CORRECTION

PATENT NO. : 6,521,403 B1
DATED : February 18, 2003
INVENTOR(S) : Maertens et al.

It is certified that error appears in the above-identified patent and that said Letters Patent is hereby corrected as shown below:

Title page,
Item [75], Inventors, delete "Melsen" and insert -- Merelbeke -- therefor.
Item [56], References Cited, FOREIGN PATENT DOCUMENTS, insert,
-- DE 420915 A 1/1993 -- after "WO 96 40764 A"
Item [57], ABSTRACT,
Line 2, delete "we," and insert -- were -- therefor.

Column 2,
Line 50, delete "Kashiwakutna" and insert -- Kashiwakuma -- therefor.

Column 3,
Line 26, delete "protein. and" and insert -- protein, and --.
Line 59, delete "kit More" and insert -- kit. More -- therefor.

Column 4,
Line 46, delete "3-amino-9-ethy]-carbazole" and insert -- 3-amino-9-ethyl-carbazole -- therefor.

Column 6,
Line 35, delete "fluid. or" and insert -- fluid, or -- therefor.

Column 7,
Line 39, delete "aa316-324" and insert -- aa316-325 -- therefor.

Column 8,
Line 23, delete "and 396-415," and insert -- and aa396-415. -- therefor.
Line 33, delete "diabodies. triabodies" and insert -- diabodies, triabodies -- therefor.
Line 42, delete "above In" and insert -- above. In -- therefor.

Column 9,
Line 25, delete "by, recombinant" and insert -- by recombinant -- therefor.
Line 26, delete "vraccinia" and insert -- vaccinia -- therefor.
Line 42, delete "protocols. see" and insert -- protocols, see -- therefor.
Line 51, delete "This-staining" and insert -- This staining -- therefor.

Column 11,
Line 8 (in the Table), delete "215.212" and insert -- 215,212 -- therefor.
Line 11, delete "SEQ ID9" and insert -- SEQ ID 29 -- therefor.

UNITED STATES PATENT AND TRADEMARK OFFICE
CERTIFICATE OF CORRECTION

PATENT NO. : 6,521,403 B1
DATED : February 18, 2003
INVENTOR(S) : Maertens et al.

It is certified that error appears in the above-identified patent and that said Letters Patent is hereby corrected as shown below:

Column 12,
Line 49, delete "Lang" and insert -- Liang -- therefor.

Column 13,
Line 10 of the Table 1, delete "IQVKNASGIYHLTNDCSNSSIVFEAETMILHLFGC" and insert -- IQVKNASGIYHLTNDCSNSSIVFEAETMILHLPGC -- therefore.
Line 13 of the Table 1, delete "VRENNSSRCWVALTPTLAARNASVPTTTIRTUIVD" and insert -- VRENNSSRCWVALTPTLAARNASVPTTTIRRHVD --.
After line 16 of Table 1, insert, as a new line -- E2 peptides --.
Line 23 of the Table 1, delete "SQVCGPVYCFTPSPVVVGTTTDRFGVPTYNWG" and insert -- SQVCGPVYCFTPSPVVVGTTDRFGVPTYNWG -- therefor.
Line 28, of the Table 1, delete "EAACNWTRGERCDLEDRDRSELSPLLLSTTLWQ" and insert -- EAACNWTRGERCDLEDRDRSELSPLLLSTTEWQ -- therefor.
Line 32 of the Table 1, delete "ARNARTLTGMFSLGARQKIQLINT" and insert -- AHNARTLTGMFSLGARQKIQLINT -- therefor.

Column 14,
Line 18 of Table 1, in the column headed "#" delete "1113" and insert -- 1173 -- therefor.

Column 29,
Line 7, delete "varient" and insert therefor -- variant --.

Signed and Sealed this

Thirteenth Day of December, 2005

JON W. DUDAS
*Director of the United States Patent and Trademark Office*

SEQUENCE LISTING

<160> NUMBER OF SEQ ID NOS: 41

<210> SEQ ID NO 1
<211> LENGTH: 35
<212> TYPE: PRT
<213> ORGANISM: Hepatitis C virus

<400> SEQUENCE: 1

```
    Tyr Glu Val Arg Asn Val Ser Gly Ile Tyr His Val Thr Asn Asp Cys
     1               5                  10                  15
    Ser Asn Ser Ser Ile Val Tyr Glu Ala Ala Asp Met Ile Met His Thr
                20                  25                  30
    Pro Gly Cys
            35
```

<210> SEQ ID NO 2
<211> LENGTH: 29
<212> TYPE: PRT
<213> ORGANISM: Hepatitis C virus

<400> SEQUENCE: 2

Ile Val Tyr Glu Ala Ala Asp Met Ile Met His Thr Pro Gly Cys Val
 1               5                  10                  15
Pro Cys Val Arg Glu Asn Asn Ser Ser Arg Cys Trp Val
            20                  25

<210> SEQ ID NO 3
<211> LENGTH: 34
<212> TYPE: PRT
<213> ORGANISM: Hepatitis C virus

<400> SEQUENCE: 3

Val Arg Glu Asn Asn Ser Ser Arg Cys Trp Val Ala Leu Thr Pro Thr
 1               5                  10                  15
Leu Ala Ala Arg Asn Ala Ser Val Pro Thr Thr Thr Ile Arg Arg His
            20                  25                  30
Val Asp

<210> SEQ ID NO 4
<211> LENGTH: 30
<212> TYPE: PRT
<213> ORGANISM: Hepatitis C virus

<400> SEQUENCE: 4

His Val Asp Leu Leu Val Gly Ala Ala Ala Phe Cys Ser Ala Met Tyr
 1               5                  10                  15
Val Gly Asp Leu Cys Gly Ser Val Phe Leu Val Ser Gln Leu
            20                  25                  30

<210> SEQ ID NO 5
<211> LENGTH: 40
<212> TYPE: PRT
<213> ORGANISM: Hepatitis C virus

<400> SEQUENCE: 5

Ser Gln Leu Phe Thr Ile Ser Pro Arg Arg His Glu Thr Val Gln Asp
 1               5                  10                  15
Cys Asn Cys Ser Ile Tyr Pro Gly His Ile Thr Gly His Arg Met Ala
            20                  25                  30
Trp Asp Met Met Met Asn Trp Ser
            35                  40

<210> SEQ ID NO 6
<211> LENGTH: 34
<212> TYPE: PRT
<213> ORGANISM: Hepatitis C virus

<400> SEQUENCE: 6

Ser Ile Tyr Pro Gly His Ile Thr Gly His Arg Met Ala Trp Asp Met
 1               5                  10                  15
Met Met Asn Trp Ser Pro Thr Thr Ala Leu Val Val Ser Gln Leu Leu
            20                  25                  30
Arg Ile

<210> SEQ ID NO 7
<211> LENGTH: 32
<212> TYPE: PRT
<213> ORGANISM: Hepatitis C virus

<400> SEQUENCE: 7

His Thr Arg Val Ser Gly Gly Ala Ala Ala Ser Asn Thr Arg Gly Leu

```
        1               5                  10                  15
        Val Ser Leu Phe Ser Pro Gly Ser Ala Gln Lys Ile Gln Leu Val Asn
                        20                  25                  30
```

<210> SEQ ID NO 8
<211> LENGTH: 34
<212> TYPE: PRT
<213> ORGANISM: Hepatitis C virus

<400> SEQUENCE: 8

```
        Asn Thr Arg Gly Leu Val Ser Leu Phe Ser Pro Gly Ser Ala Gln Lys
        1               5                  10                  15
        Ile Gln Leu Val Asn Thr Asn Gly Ser Trp His Ile Asn Arg Thr Ala
                        20                  25                  30
        Leu Asn
```

<210> SEQ ID NO 9
<211> LENGTH: 35
<212> TYPE: PRT
<213> ORGANISM: Hepatitis C virus

<400> SEQUENCE: 9

```
        Leu Val Asn Thr Asn Gly Ser Trp His Ile Asn Arg Thr Ala Leu Asn
        1               5                  10                  15
        Cys Asn Asp Ser Leu Gln Thr Gly Phe Phe Ala Ala Leu Phe Tyr Lys
                        20                  25                  30
        His Lys Phe
                 35
```

<210> SEQ ID NO 10
<211> LENGTH: 38
<212> TYPE: PRT
<213> ORGANISM: Hepatitis C virus

<400> SEQUENCE: 10

```
        Asn Asp Ser Leu Gln Thr Gly Phe Phe Ala Ala Leu Phe Tyr Lys His
        1               5                  10                  15
        Lys Phe Asn Ser Ser Gly Cys Pro Glu Arg Leu Ala Ser Cys Arg Ser
                        20                  25                  30
        Ile Asp Lys Phe Ala Gln
                 35
```

<210> SEQ ID NO 11
<211> LENGTH: 28
<212> TYPE: PRT
<213> ORGANISM: Hepatitis C virus

<400> SEQUENCE: 11

```
        Arg Ser Ile Asp Lys Phe Ala Gln Gly Trp Gly Pro Leu Thr Tyr Thr
        1               5                  10                  15
        Glu Pro Asn Ser Ser Asp Gln Arg Pro Tyr Cys Trp
                        20                  25
```

<210> SEQ ID NO 12
<211> LENGTH: 34
<212> TYPE: PRT
<213> ORGANISM: Hepatitis C virus

<400> SEQUENCE: 12

```
        Ser Asp Gln Arg Pro Tyr Cys Trp His Tyr Ala Pro Arg Pro Cys Gly
        1               5                  10                  15
        Ile Val Pro Ala Ser Gln Val Cys Gly Pro Val Tyr Cys Phe Thr Pro
                        20                  25                  30
        Ser Pro
```

<210> SEQ ID NO 13
<211> LENGTH: 31
<212> TYPE: PRT

-continued

```
<213> ORGANISM: Hepatitis C virus

<400> SEQUENCE: 13

Ser Gln Val Cys Gly Pro Val Tyr Cys Phe Thr Pro Ser Pro Val Val
  1               5                  10                  15
Val Gly Thr Thr Asp Arg Phe Gly Val Pro Thr Tyr Asn Trp Gly
             20                  25                  30

<210> SEQ ID NO 14
<211> LENGTH: 44
<212> TYPE: PRT
<213> ORGANISM: Hepatitis C virus

<400> SEQUENCE: 14

Gly Val Pro Thr Tyr Asn Trp Gly Ala Asn Asp Ser Asp Val Leu Ile
  1               5                  10                  15
Leu Asn Asn Thr Arg Pro Pro Arg Gly Asn Trp Phe Gly Cys Thr Trp
             20                  25                  30
Met Asn Gly Thr Gly Phe Thr Lys Thr Cys Gly Gly
         35                  40

<210> SEQ ID NO 15
<211> LENGTH: 30
<212> TYPE: PRT
<213> ORGANISM: Hepatitis C virus

<400> SEQUENCE: 15

Thr Lys Thr Cys Gly Gly Pro Pro Cys Asn Ile Gly Gly Ala Gly Asn
  1               5                  10                  15
Asn Thr Leu Thr Cys Pro Thr Asp Cys Phe Arg Lys His Pro
             20                  25                  30

<210> SEQ ID NO 16
<211> LENGTH: 45
<212> TYPE: PRT
<213> ORGANISM: Hepatitis C virus

<400> SEQUENCE: 16

Thr Asp Cys Phe Arg Lys His Pro Glu Ala Thr Tyr Ala Arg Cys Gly
  1               5                  10                  15
Ser Gly Pro Trp Leu Thr Pro Arg Cys Met Val His Tyr Pro Tyr Arg
             20                  25                  30
Leu Trp His Tyr Pro Cys Thr Val Asn Phe Thr Ile Phe
         35                  40                  45

<210> SEQ ID NO 17
<211> LENGTH: 28
<212> TYPE: PRT
<213> ORGANISM: Hepatitis C virus

<400> SEQUENCE: 17

Thr Val Asn Phe Thr Ile Phe Lys Val Arg Met Tyr Val Gly Gly Val
  1               5                  10                  15
Glu His Arg Phe Glu Ala Ala Cys Asn Trp Thr Arg
             20                  25

<210> SEQ ID NO 18
<211> LENGTH: 33
<212> TYPE: PRT
<213> ORGANISM: Hepatitis C virus

<400> SEQUENCE: 18

Glu Ala Ala Cys Asn Trp Thr Arg Gly Glu Arg Cys Asp Leu Glu Asp
  1               5                  10                  15
Arg Asp Arg Ser Glu Leu Ser Pro Leu Leu Leu Ser Thr Thr Glu Trp
             20                  25                  30
Gln
```

<210> SEQ ID NO 19
<211> LENGTH: 23
<212> TYPE: PRT
<213> ORGANISM: Hepatitis C virus

<400> SEQUENCE: 19

```
Lys Thr Thr Asn Arg Leu Val Ser Met Phe Ala Ser Gly Pro Lys Gln
 1               5                  10                  15
Asn Val His Leu Ile Asn Thr
            20
```

<210> SEQ ID NO 20
<211> LENGTH: 23
<212> TYPE: PRT
<213> ORGANISM: Hepatitis C virus

<400> SEQUENCE: 20

```
His Thr Thr Ser Thr Leu Ala Ser Leu Phe Ser Pro Gly Ala Ser Gln
 1               5                  10                  15
Arg Ile Gln Leu Val Asn Thr
            20
```

<210> SEQ ID NO 21
<211> LENGTH: 23
<212> TYPE: PRT
<213> ORGANISM: Hepatitis C virus

<400> SEQUENCE: 21

```
His Val Thr Cys Thr Leu Thr Ser Leu Phe Arg Pro Gly Ala Ser Gln
 1               5                  10                  15
Lys Ile Gln Leu Val Asn Thr
            20
```

<210> SEQ ID NO 22
<211> LENGTH: 24
<212> TYPE: PRT
<213> ORGANISM: Hepatitis C virus

<400> SEQUENCE: 22

```
Ala His Asn Ala Arg Thr Leu Thr Gly Met Phe Ser Leu Gly Ala Arg
 1               5                  10                  15
Gln Lys Ile Gln Leu Ile Asn Thr
            20
```

<210> SEQ ID NO 23
<211> LENGTH: 23
<212> TYPE: PRT
<213> ORGANISM: Hepatitis C virus

<400> SEQUENCE: 23

```
Ser Asp Thr Arg Gly Leu Val Ser Leu Phe Ser Pro Gly Ser Ala Gln
 1               5                  10                  15
Lys Ile Gln Leu Val Asn Thr
            20
```

<210> SEQ ID NO 24
<211> LENGTH: 23
<212> TYPE: PRT
<213> ORGANISM: Hepatitis C virus

<400> SEQUENCE: 24

```
Ser Ser Thr Gln Ser Leu Val Ser Trp Leu Ser Gln Gly Pro Ser Gln
 1               5                  10                  15
Lys Ile Gln Leu Val Asn Thr
            20
```

```
<210> SEQ ID NO 25
<211> LENGTH: 23
<212> TYPE: PRT
<213> ORGANISM: Hepatitis C virus

<400> SEQUENCE: 25

His Thr Met Thr Gly Ile Val Arg Phe Phe Ala Pro Gly Pro Lys Gln
    1               5                   10                  15
    Asn Val His Leu Ile Asn Thr
                20

<210> SEQ ID NO 26
<211> LENGTH: 23
<212> TYPE: PRT
<213> ORGANISM: Hepatitis C virus

<400> SEQUENCE: 26

Arg Ala Met Ser Gly Leu Val Ser Leu Phe Thr Pro Gly Ala Lys Gln
    1               5                   10                  15
    Asn Ile Gln Leu Ile Asn Thr
                20

<210> SEQ ID NO 27
<211> LENGTH: 23
<212> TYPE: PRT
<213> ORGANISM: Hepatitis C virus

<400> SEQUENCE: 27

His Val Thr Gly Thr Leu Thr Ser Leu Phe Arg Pro Gly Ala Ser Gln
    1               5                   10                  15
    Lys Ile Gln Leu Val Asn Thr
                20

<210> SEQ ID NO 28
<211> LENGTH: 23
<212> TYPE: PRT
<213> ORGANISM: Hepatitis C virus

<400> SEQUENCE: 28

Arg Thr Thr Gln Gly Leu Val Ser Leu Phe Ser Arg Gly Ala Lys Gln
    1               5                   10                  15
    Asp Ile Gln Leu Ile Asn Thr
                20

<210> SEQ ID NO 29
<211> LENGTH: 15
<212> TYPE: PRT
<213> ORGANISM: Hepatitis C virus

<400> SEQUENCE: 29

Ile Val Tyr Glu Ala Ala Asp Met Ile Met His Thr Pro Gly Cys
    1               5                   10                  15

<210> SEQ ID NO 30
<211> LENGTH: 20
<212> TYPE: PRT
<213> ORGANISM: Hepatitis C virus

<400> SEQUENCE: 30

Ser Ile Tyr Pro Gly His Ile Thr Gly His Arg Met Ala Trp Asp Met
    1               5                   10                  15
    Met Met Asn Trp
                20

<210> SEQ ID NO 31
<211> LENGTH: 21
<212> TYPE: PRT
```

-continued

```
<213> ORGANISM: Hepatitis C virus

<400> SEQUENCE: 31

Asn Thr Arg Gly Leu Val Ser Leu Phe Ser Pro Gly Ser Ala Gln Lys
      1               5                   10                  15
      Ile Gln Leu Val Asn
                  20

<210> SEQ ID NO 32
<211> LENGTH: 35
<212> TYPE: PRT
<213> ORGANISM: Hepatitis C virus

<400> SEQUENCE: 32

Tyr Gln Val Arg Asn Ser Thr Gly Leu Tyr His Val Thr Asn Asp Cys
      1               5                   10                  15
      Pro Asn Ser Ser Ile Val Tyr Glu Ala Asp Ala Ile Leu His Thr
                  20                  25                  30
      Pro Gly Cys
              35

<210> SEQ ID NO 33
<211> LENGTH: 35
<212> TYPE: PRT
<213> ORGANISM: Hepatitis C virus

<400> SEQUENCE: 33

Val Glu Val Lys Asn Asn Ser Asn Ser Tyr Met Ala Thr Asn Asp Cys
      1               5                   10                  15
      Ser Asn Ser Ser Ile Ile Trp Gln Leu Glu Gly Ala Val Leu His Thr
                  20                  25                  30
      Pro Gly Cys
              35

<210> SEQ ID NO 34
<211> LENGTH: 35
<212> TYPE: PRT
<213> ORGANISM: Hepatitis C virus

<400> SEQUENCE: 34

Val Glu Val Lys Asn Thr Ser Thr Ser Tyr Met Val Thr Asn Asp Cys
      1               5                   10                  15
      Ser Asn Ser Ser Ile Val Trp Gln Leu Glu Gly Ala Val Leu His Thr
                  20                  25                  30
      Pro Gly Cys
              35

<210> SEQ ID NO 35
<211> LENGTH: 35
<212> TYPE: PRT
<213> ORGANISM: Hepatitis C virus

<400> SEQUENCE: 35

Leu Glu Trp Arg Asn Thr Ser Gly Leu Tyr Val Leu Thr Asn Asp Cys
      1               5                   10                  15
      Ser Asn Ser Ser Ile Val Tyr Glu Ala Asp Asp Val Ile Leu His Thr
                  20                  25                  30
      Pro Gly Cys
              35

<210> SEQ ID NO 36
<211> LENGTH: 35
<212> TYPE: PRT
<213> ORGANISM: Hepatitis C virus

<400> SEQUENCE: 36

Ile Asn Tyr Arg Asn Val Ser Gly Ile Tyr His Val Thr Asn Asp Cys
      1               5                   10                  15
```

```
        Pro Asn Ser Ser Ile Val Tyr Glu Ala Asp His His Ile Leu His Leu
                        20                  25                  30
            Pro Gly Cys
                    35

<210> SEQ ID NO 37
<211> LENGTH: 35
<212> TYPE: PRT
<213> ORGANISM: Hepatitis C virus

<400> SEQUENCE: 37

Val Pro Tyr Arg Asn Ala Ser Gly Ile Tyr His Ile Thr Asn Asp Cys
            1               5                   10                  15
            Pro Asn Ser Ser Ile Val Tyr Glu Ala Asp Asn Leu Ile Leu His Ala
                        20                  25                  30
            Pro Gly Cys
                    35

<210> SEQ ID NO 38
<211> LENGTH: 35
<212> TYPE: PRT
<213> ORGANISM: Hepatitis C virus

<400> SEQUENCE: 38

Leu Thr Tyr Gly Asn Ser Ser Gly Leu Tyr His Leu Thr Asn Asp Cys
            1               5                   10                  15
            Ser Asn Ser Ser Ile Val Leu Glu Ala Asp Ala Met Ile Leu His Leu
                        20                  25                  30
            Pro Gly Cys
                    35

<210> SEQ ID NO 39
<211> LENGTH: 34
<212> TYPE: PRT
<213> ORGANISM: Hepatitis C virus

<400> SEQUENCE: 39

Leu Asn Tyr Ala Asn Lys Ser Gly Leu Tyr His Leu Thr Asn Asp Cys
            1               5                   10                  15
            Pro Asn Ser Ser Ile Val Tyr Glu Ala Asn Gly Met Ile Leu His Leu
                        20                  25                  30
            Pro Gly

<210> SEQ ID NO 40
<211> LENGTH: 35
<212> TYPE: PRT
<213> ORGANISM: Hepatitis C virus

<400> SEQUENCE: 40

Ile Gln Val Lys Asn Ala Ser Gly Ile Tyr His Leu Thr Asn Asp Cys
            1               5                   10                  15
            Ser Asn Ser Ser Ile Val Phe Glu Ala Glu Thr Met Ile Leu His Leu
                        20                  25                  30
            Pro Gly Cys
                    35

<210> SEQ ID NO 41
<211> LENGTH: 35
<212> TYPE: PRT
<213> ORGANISM: Hepatitis C virus

<400> SEQUENCE: 41

Leu Glu Tyr Arg Asn Ala Ser Gly Leu Tyr Met Val Thr Asn Asp Cys
            1               5                   10                  15
            Ser Asn Gly Ser Ile Val Tyr Glu Ala Gly Asp Ile Ile Leu His Leu
                        20                  25                  30
            Pro Gly Cys
                    35
```